United States Patent [19]

Lu

[11] Patent Number: 5,591,214
[45] Date of Patent: Jan. 7, 1997

[54] PACEMAKER WITH AUTOMATIC BLANKING PERIOD FUNCTION

[75] Inventor: Richard Lu, Highlands Ranch, Colo.

[73] Assignee: Telectronics Pacing Systems, Inc., Englewood, Colo.

[21] Appl. No.: 560,733

[22] Filed: Nov. 20, 1995

[51] Int. Cl.⁶ ..................................................... A61N 1/00
[52] U.S. Cl. ................................................................ 607/9
[58] Field of Search .............................. 607/4, 9, 27, 28, 607/11

[56] References Cited

U.S. PATENT DOCUMENTS 4,974,589   12/1990   Sholder ........................................ 607/9

*Primary Examiner*—Marvin M. Lateef
*Assistant Examiner*—Scott M. Getzow
*Attorney, Agent, or Firm*—Gottlieb, Rackman & Reisman

[57] ABSTRACT

The blanking periods for an implantable cardiac device, such as a pacemaker, is determined by providing an excitation in a cardiac chamber and monitoring the corresponding cardiac activity. For in-channel blanking periods, the response from the same chamber is monitored while for cross-channel blanking period, the other cardiac chamber is monitored. The optimal blanking period is then determined based on the cardiac activity. This period is programmed directly into the device, or transmitted to an external programmer where it is used to provide guidance to a health care professional. The optimal blanking period duration may also be determined using other signals sensed by the programmer, using ECG's or MTE's.

17 Claims, 7 Drawing Sheets

PACEMAKER WITH AUTOMATIC BLANKING PERIOD FUNCTION

FIELD OF THE INVENTION

This invention relates to single or dual chamber pacemakers, and more particularly to a mode of operation wherein one or more blanking periods are determined by measuring inherent noise propagation characteristics of the pacemaker system.

BACKGROUND OF THE INVENTION

In the following description, the term pacemaker refers to all implantable cardiac devices having cardiac pacing and sensing capabilities. Briefly, in these types of devices the sensed signals are fed to a sensing amplifier for amplification and signal conditioning.

This sensing amplifier disables its sensing ability for a brief period following a sensed or a paced event. The time during which sensing is disabled is called a blanking period. The blanking period prevents inappropriate sensing of residual energy by the pacemaker amplifier following an intrinsic event or a pacemaker output pulse. The blanking period may be applied to the same chamber where the event occurs. In dual chamber pacemakers, the blanking period also may be applied to the chamber other than the one in which the event occurs. In this case, the blanking period is called the cross-channel blanking period. There are eight possible blanking periods (See FIG. 1A) in a pacemaker: (1) atrial blanking period after an atrial sense, (2) atrial blanking period after an atrial pace, (3) atrial blanking period after a ventricular sense, (4) atrial blanking period after a ventricular pace, (5) ventricular blanking period after an atrial sense, (6) ventricular blanking period after an atrial pace (7) ventricular blanking period after a ventricular sense, and (8) ventricular blanking period after a ventricular pace. The blanking period is a function of sensing/pacing polarity; sensitivity; pacing amplitude, pulse width, lead maturation, and position of leads. In general, in prior art devices, the durations of these blanking periods was either fixed at the factory, or was one of the adjustable programmer parameters that had to be set by the physician either based on average values obtained from statistical data, or by trial and error.

It is advantageous to provide dual chamber pacemaker with an AMS (Automatic Mode Switching) function, as described for example, in U.S. Pat. No. 5,441,523, incorporated herein by reference. The AMS function switches the pacemaker from a rate-response mode, wherein pacing rate is determined from a physiological pacemaker to a backup pacing rate under certain pre-selected conditions. However, in such a pacemaker an extra long atrial blanking period reduces the sensitivity of the AMS function. In the worst case situation the A-V delay may be equal to or shorter than the atrial blanking period following an atrial event (blanking periods (1) or (2)). Since the A-V delay is followed by a ventricular event, which in turn causes the atrial blanking period to extend still further by a cross channel blanking period (3) or (4). If an intrinsic R-wave occurs before the end of the A-V delay, the atrial blanking period is also extended by blanking period (3). Therefore, fast atrial events associated with atrial tachycardia such as atrial fibrillation or atrial flutter may occur during this extra long blanking period and cannot be sensed by the pacemaker. Accordingly the atrial tachycardia is not detected and the pacemaker does not activate the AMS function to switch from a dual chamber to a ventricular non-tracking mode.

However, if the blanking periods are set to be too short, in channel or cross channel noise may be erroneously sensed as a cardiac event. For example for a short atrial blanking following a ventricular event, a farfield R wave may be sensed improperly as a new ventricular event.

Similarly, if a cross channel ventricular blanking period (5 or 6) is too short, an atrial event may be erroneously interpreted as a ventricular event and ventricular pacing maybe inhibited. If the same ventricular blanking period is too long however, a premature ventricular contraction may occur during this blanking period and a proper A-V delay would not be set up.

Thus, it is clear that the operation of a pacemaker would be vastly improved if the blanking periods can be set accurately and automatically to reflect and compensate for the electrical characteristics of a particular pacemaker system and/or the patient's tissues.

OBJECTIVES AND ADVANTAGES OF THE INVENTION

An objective of the present invention is to provide a pacemaker in which the sensing blanking periods are optimized for a particular patient, pacemaker or both.

A further objective is to provide a pacemaker system in which the blanking periods are determined automatically.

A further objective is to provide a pacemaker system capable of calculating both the in channel and cross channel blanking periods.

Other objectives and advantages of the invention shall become apparent from the following description.

Briefly, a pacemaker system constructed in accordance with this invention includes a pacemaker having means for generating test pulses to a cardiac chamber, and means for sensing cardiac signals corresponding to said pulses, after a preset time period. The time period required for said cardiac signals to decay is measured and this period is used to determine the duration of the in-channel and/or cross channel blanking periods for the pacemaker.

Alternatively, the duration of the blanking periods is determined externally in which case the cardiac response to other stimulation is used as a criteria.

BRIEF DESCRIPTION OF THE DRAWINGS

Further objects, features and advantages of the invention will become apparent upon consideration of the following description, taken in conjunction with the accompanying drawing, in which:

FIG. 1A shows the blanking periods in a prior art dual chamber pacemaker;

DETAILED DESCRIPTION OF THE INVENTION

Figure 1:
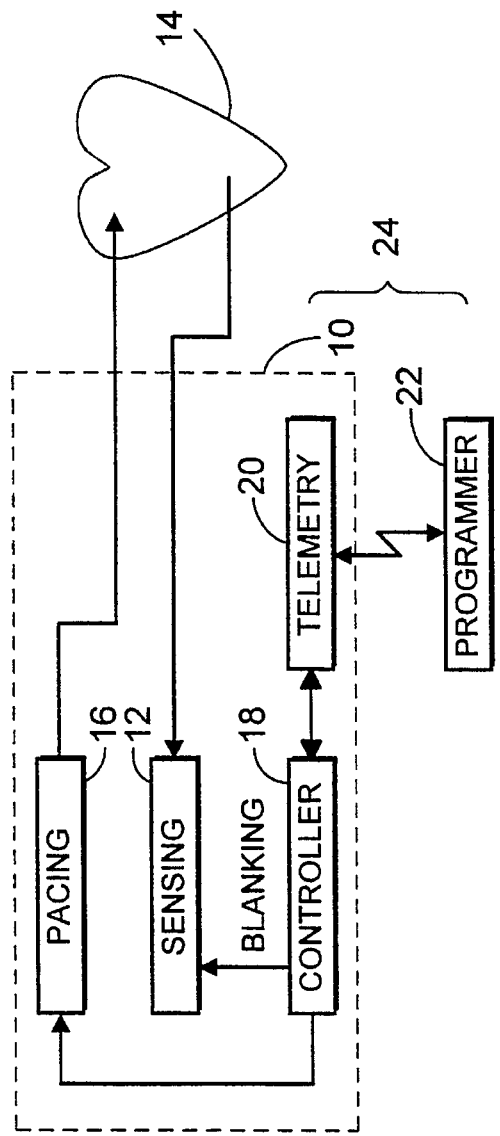
FIG. 1 is a block diagram of a pacemaker which embodies the subject invention.

Referring now to FIG. 1, a pacemaker 10 constructed in accordance with this invention includes a sensing circuit 12 receiving signals from the heart 14 of a patient and a pacing circuit 16 for generating pacing pulses for the heart 14. A controller 18, which is usually a digital microprocessor receives the signals from the sensor indicative of the electrical activity of the heart, and based on these signals, generates appropriate control signals for the pacing circuit 16.

Pacemaker 10 further includes a telemetry device 20 for selectively exchanging information with an external programmer 22. The pacemaker 10 and programmer 22 jointly form a pacemaker system 24.

Figure 2:
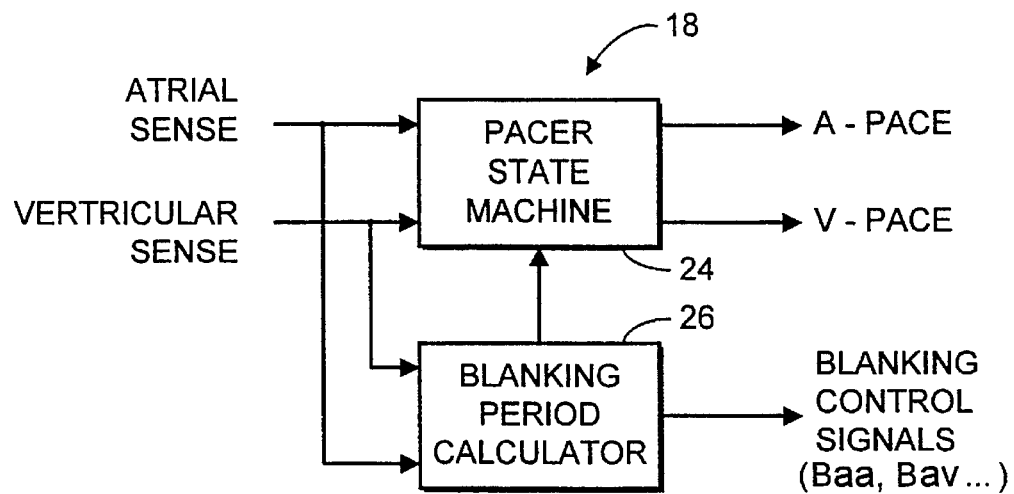
FIG. 2 is a block diagram of the controller of FIG. 1.

Although the invention may be applicable to other types of pacemakers, the pacemaker in FIG. 2 is adapted to operate in a DDDR mode and as such, it receives A-sense and V-sense signals and generates A-pace and V-pace pulses. As shown in more detail in FIG. 2, the controller 18 includes a pacer state machine 24 which generates the pace signals based on the sense signals. In addition, the A- and V-sense signals are also fed to a blanking period calculator 26 which calculates and stores the blanking periods and sends corresponding blanking period signals to the sensory circuit 12.

Figure 3:
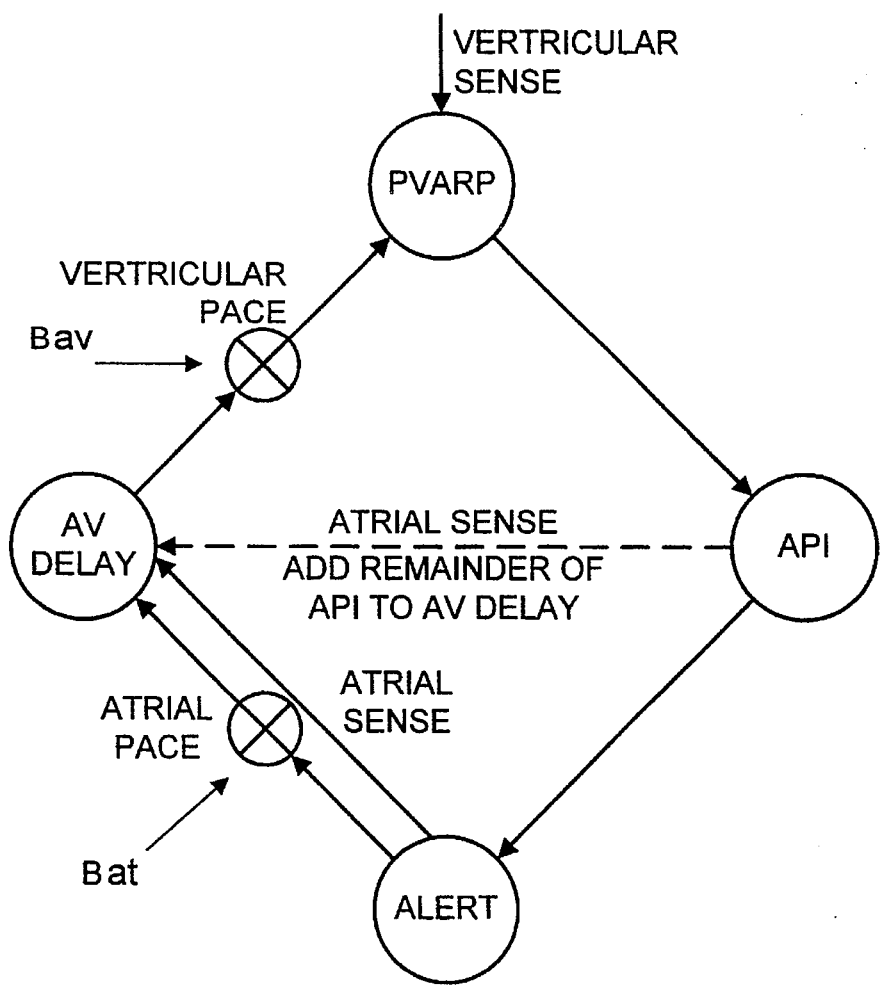
FIG. 3 is a state diagram that characterizes the operation of the pacemaker of FIG. 1.

A preferred embodiment the pacemaker state diagram is shown in FIG. 3. It should be understood that the invention is applicable to pacemakers operating in other modes as well. The PVARP is the Post Ventricular Atrial Refractory Period. An A-sense occurring during this interval is considered to be due to a retrogradely conducted ventricular event and is ignored. A V-sense occurring at any time starts the PVARP.

The API which follows the PVARP is the Atrial Protection Interval and defines the minimum time between an ignored A-sense (i.e., in the PVARP) and the next A-pace. The API is intended to prevent an A-pace being provided during the vulnerable part of the atrial repolarization period, i.e., the relative refractory period during which arrhythmias may be induced.

The Alert which may follow API, is the interval during which A-senses are classified to be P-waves (i.e., of sinus origin) within the correct rate range. Such P-waves are tracked 1:1 by the ventricular channel. The Alert is the remainder of VV interval after the sum of the AV delay plus the PVARP plus the API.

The AV delay which follows an atrial event is intended to mimic the natural P-wave to R-wave interval and is the time between an A-sense (or A-pace) and a V-pace (in the absence of a V-sense).

Figure 4:
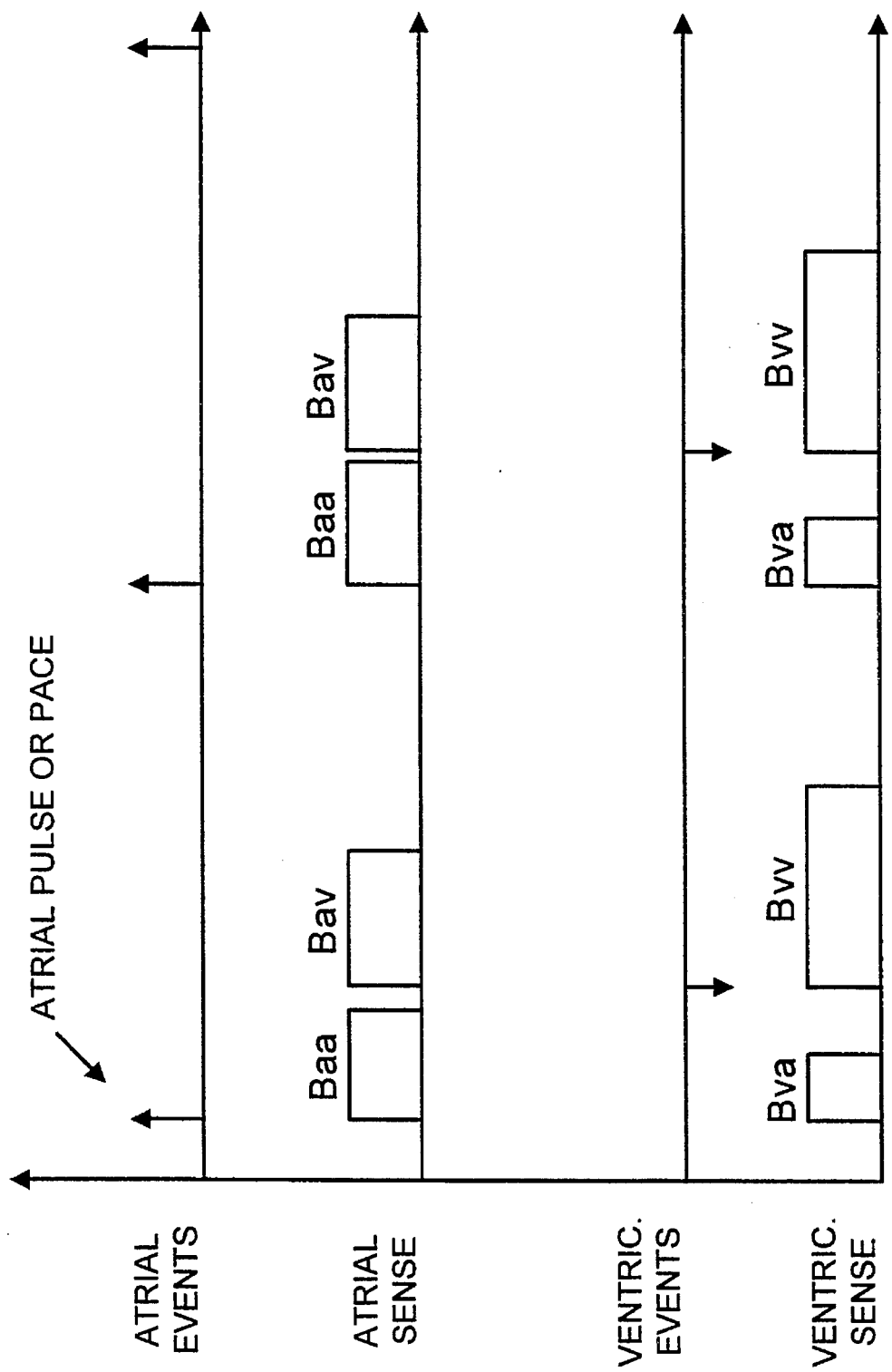
FIG. 4 is a timing diagram showing the relationship between pacing pulses and the corresponding blanking periods in accordance with this invention.

Importantly, the subject pacemaker further includes means for providing blanking periods in the various sensing channels during either atrial or ventricular activity. More particularly, as shown in FIG. 4, every atrial event (i.e., atrial pace or atrial sense) is followed in the atrial sensing channel by a blanking period. Moreover blanking periods in the atrial sensing channel also follow each ventricular event to inhibit cross-channel noise. In FIG. 4 the blanking periods for atrial sensing following an atrial event are designated as Baa, and the ones following a ventricular event are designated Bav. The corresponding blanking periods for the ventricular channel are also shown in the Figure and are designated as Bvv and Bva, as shown.

Figure 5:
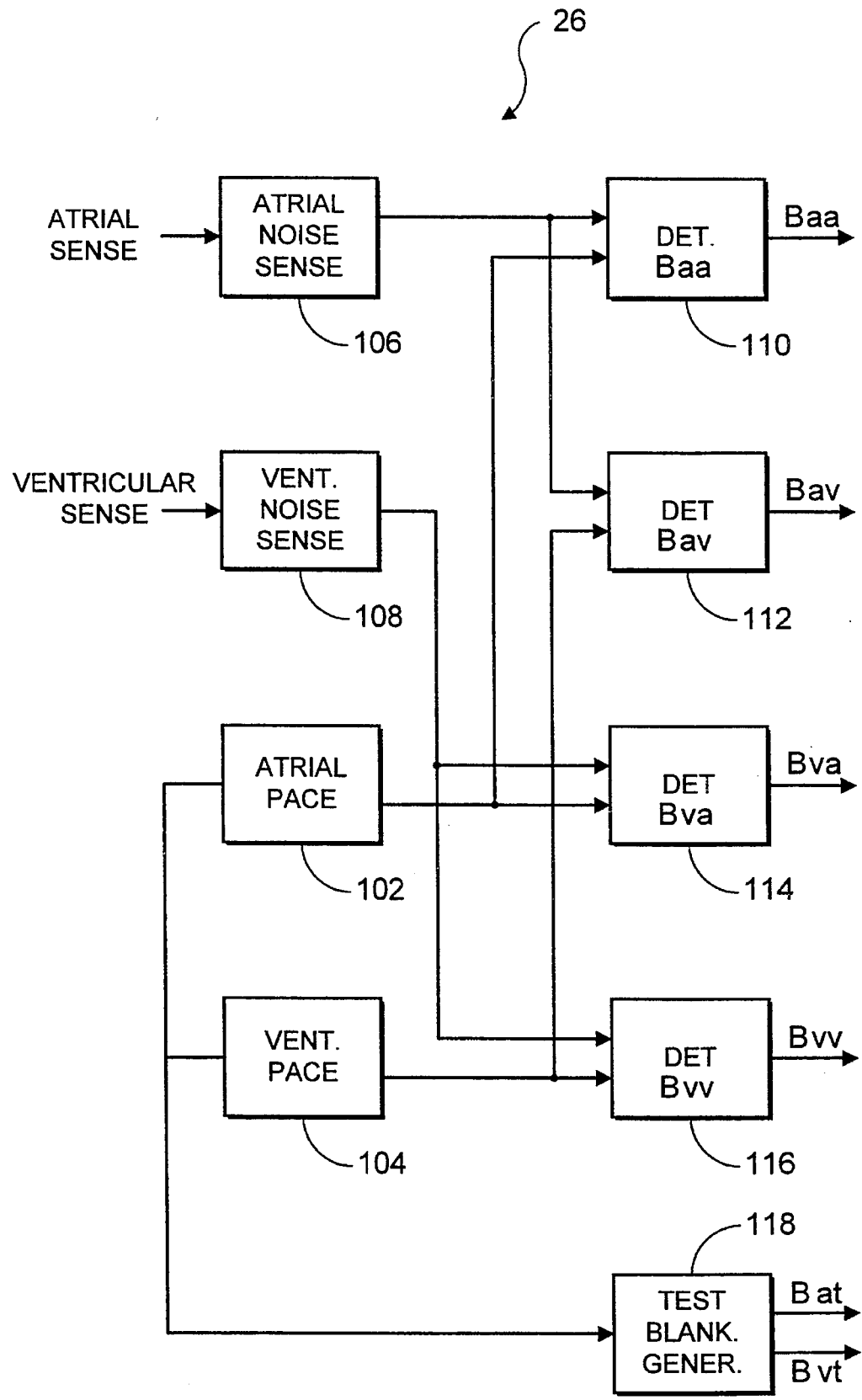
FIG. 5 shows a circuit used to determine the blanking periods in accordance with this invention.

As previously described, the present invention pertains to the means of determining and adjusting these blanking periods to insure that the sensing channels operate accurately and reliably. In order to determine these blanking periods, the pacemaker is provided with the blanking period calculator 26. As shown in detail in FIG. 5, the calculator 26 monitors the atrial and ventricular intracardiac signals and generates its own atrial and ventricular test blanking signals Bat, Bvt, respectively.

The calculator 26 includes an atrial noise sensor 106 and a ventricular noise sensor 108. These sensors receive respectively the atrial and ventricular intracardiac signals as shown in FIG. 1. The calculator 26 also includes an atrial pace command generator 102 and a ventricle pace command generator 104. The calculator 26 further includes individual determinator elements 110–116. The operation of the calculator 26 is now described in conjunction with the graphs of FIGS. 4 and 6 and the flow chart of FIG. 7.

Figure 7:
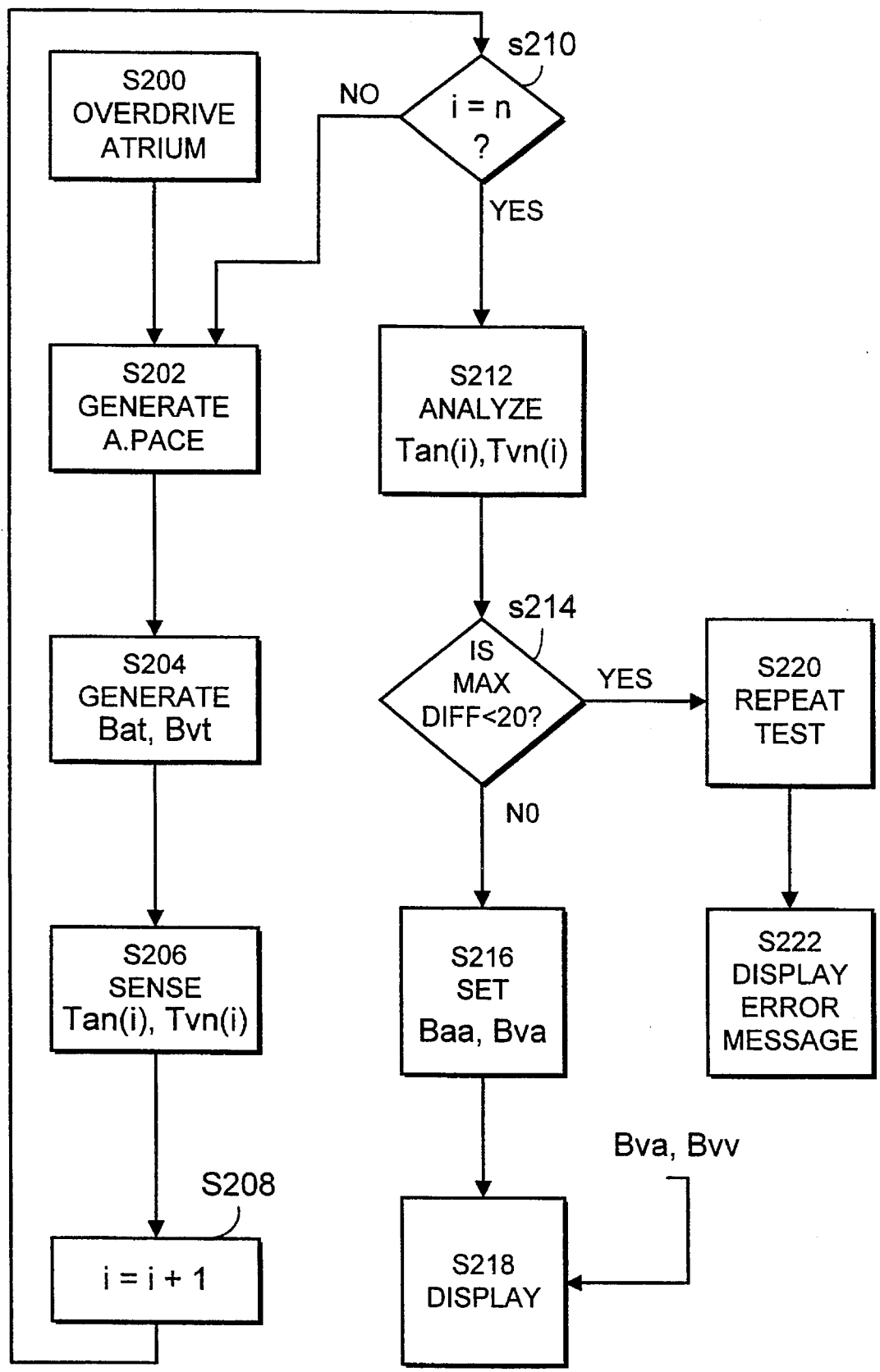
FIG. 7 shows a flow chart for the circuit of FIG. 5.

Preferably the determination for the various blanking periods is made (or modified) in a physician's office with the patient's pacemaker being coupled to the programmer 22 for initializing or modifying the pacemaker's operation. The programmer 22 provides the physicians with a sequence of steps that are performed to set up various programming parameters. As part of this procedure, the physician may measure and set the pacing signal threshold levels. The blanking periods may be determined and set at the same time as follows. Initially, as shown in FIG. 7, in step S200 the atrium is overdrive paced by issuing appropriate pacing command to generator 102 using a fixed A-V delay of 200 msec. This step is performed to insure that the blanking periods are determined in response to atrial pacing and not an atrial natural pulse. It is believed that blanking periods following a paced pulse in either chamber should be longer than the blanking periods following an intrinsic cardiac event. Therefore, it is safe to apply the blanking periods determined for a paced event to a sensed (intrinsic) event.

Figure 6:
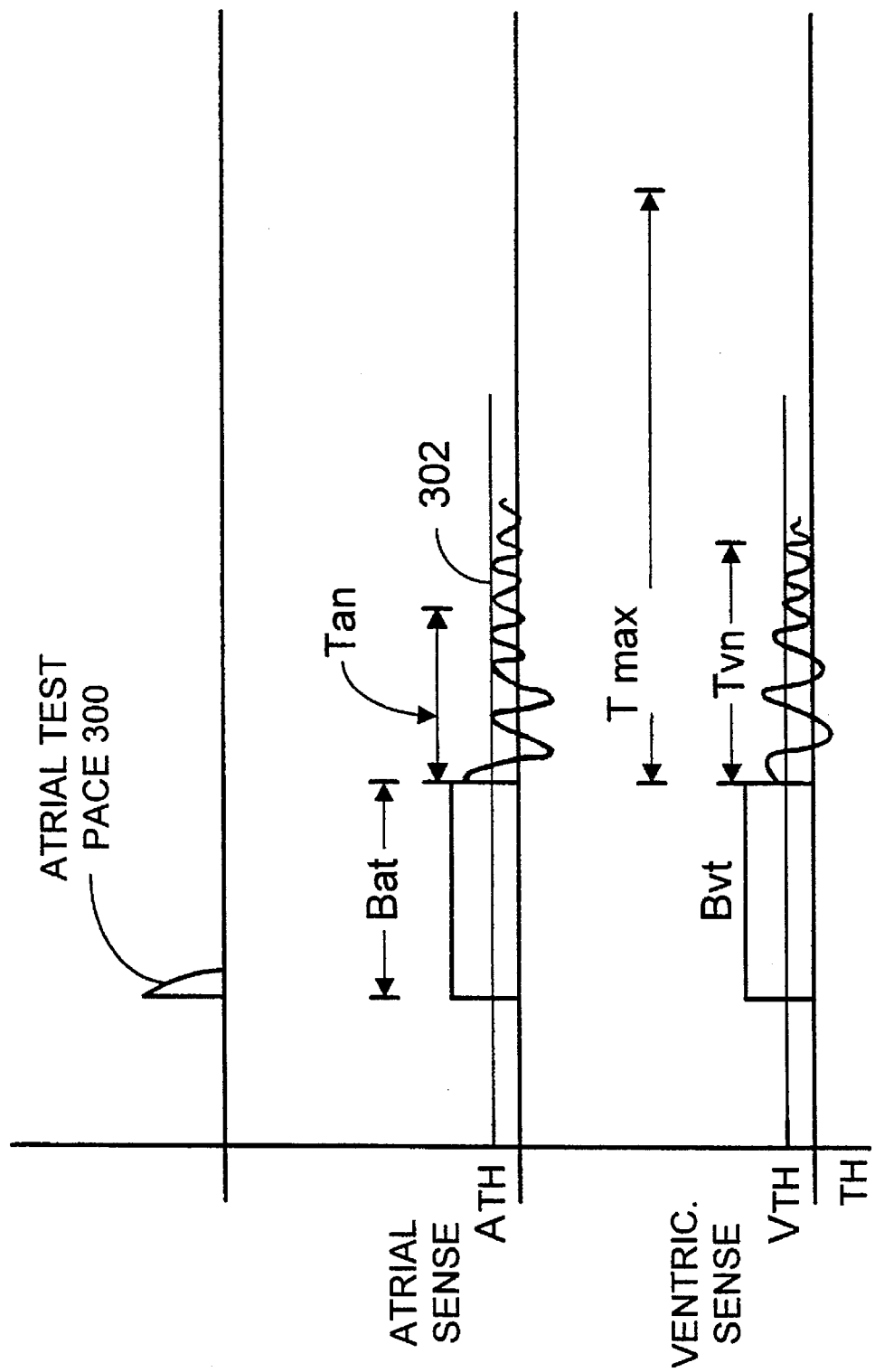
FIG. 6 shows a timing diagram for the circuit of FIG. 5.

Next an atrial test pace signal 300 is generated, as indicated on FIG. 6 (Step 202). Following this signal 300, a shortened atrial test blanking signal Bat is generated by a test blanking generator 118 (FIG. 5) for the atrial sensing channel 25. A similar signal Bvt is generated by generator 118 for the ventricular sensing channel 34 (FIG. 6, Step 204, FIG. 7). These signals are selected to correspond to the time required for the sense amplifier in sensing circuit 12, sensors 106, 108 to settle. For example these test blanking periods may be in the order of 20–30 msec.

Following the test blanking signal Bat, the atrial noise sensor 106 starts monitoring the atrial intracardiac signal. As shown in FIG. 6, typically a variable noise signal 302 is sensed in response to atrial test pace signal 300. Noise signal 302 sensed in the atrium decays after a time duration Tan at which time its peak falls below the sensor threshold level ATH. The output of atrial sensor 106 is fed to determinator 110 which also receives the Bat signal. Determinator 110 measures the time duration Tan by determining the last point in time when the atrial noise sensor receives an input exceeding ATH. This time duration Tan is characteristic of the tissues of heart and other factors.

As shown in FIG. 6, concurrently with the blanking period Bat, a corresponding blanking period Bvt is also generated for the ventricular sensor. Preferably this signal is also in the range of 20–30 msec. At the end of this period, a noise signal 304 is detected by sensing circuit 12. This signal is sensed by ventricular noise sensor 108 and fed to the determinator circuit 114. Determinator circuit 114 also receives the Bvt signal. After a time period Tvn, the ventricular noise signal decays to a peak level below threshold VTH. In order to insure that the blanking period does not exceed the A-V interval, the period Tvn is limited to 80 msec (Tmax). The determinator 114 thus measures the length of signal Tvn.

As shown on FIG. 7, after the signals Tan (i), Tvn (i) are measured, the whole cycle is repeated several times until several values Tan(n), Tvn (n) are obtained. The value of 'n' may be for example two. This is illustrated in FIG. 7 by steps S206, S208, S210. At this point, the parameters Tan(n), Tvn(0 . . . n) are analyzed to determine the maximum difference between the respective values. In step S214 a test is conducted to determine if the difference between any two of the parameters Tan is greater than 20 msec. If this difference is less than 20 msec, than the longest Tan (longest) is selected. In step S 216 the blanking period is then calculated or set by adding Bat+Tan (longest)+safety factor. For example the safety factor may be about 15 msec. The parameters Tvn(o . . . n) are analyzed similarly to determine in step S216 for the value Bav. These values are sent to the display of the programmer. (S218).

If in step S214 it is determined that the difference between any two measurement Tan (j) exceeds 20 msec, then in step S220 an error message is sent to the programmer which in response (S222) displays a request that the whole procedure be repeated since the first set of values are unreliable.

After the blanking periods Baa, and Bav are calculated as described above, the ventricle is paced in a manner similar the one described above to obtain the values for Bva and Bvv.

The value of Baa, Bav, Bva, Bvv are transmitted to and displayed by the programmer in step S218. These values may be used as parameters by the pacemaker or may be used as suggested values to the physician as possible programmed values for blanking periods. The value of Bva is not very important and has been included herein for the sake of completeness.

Alternatively, the pacemaker 24 itself may set its own blanking periods to the values determined as described above.

Figure 8:
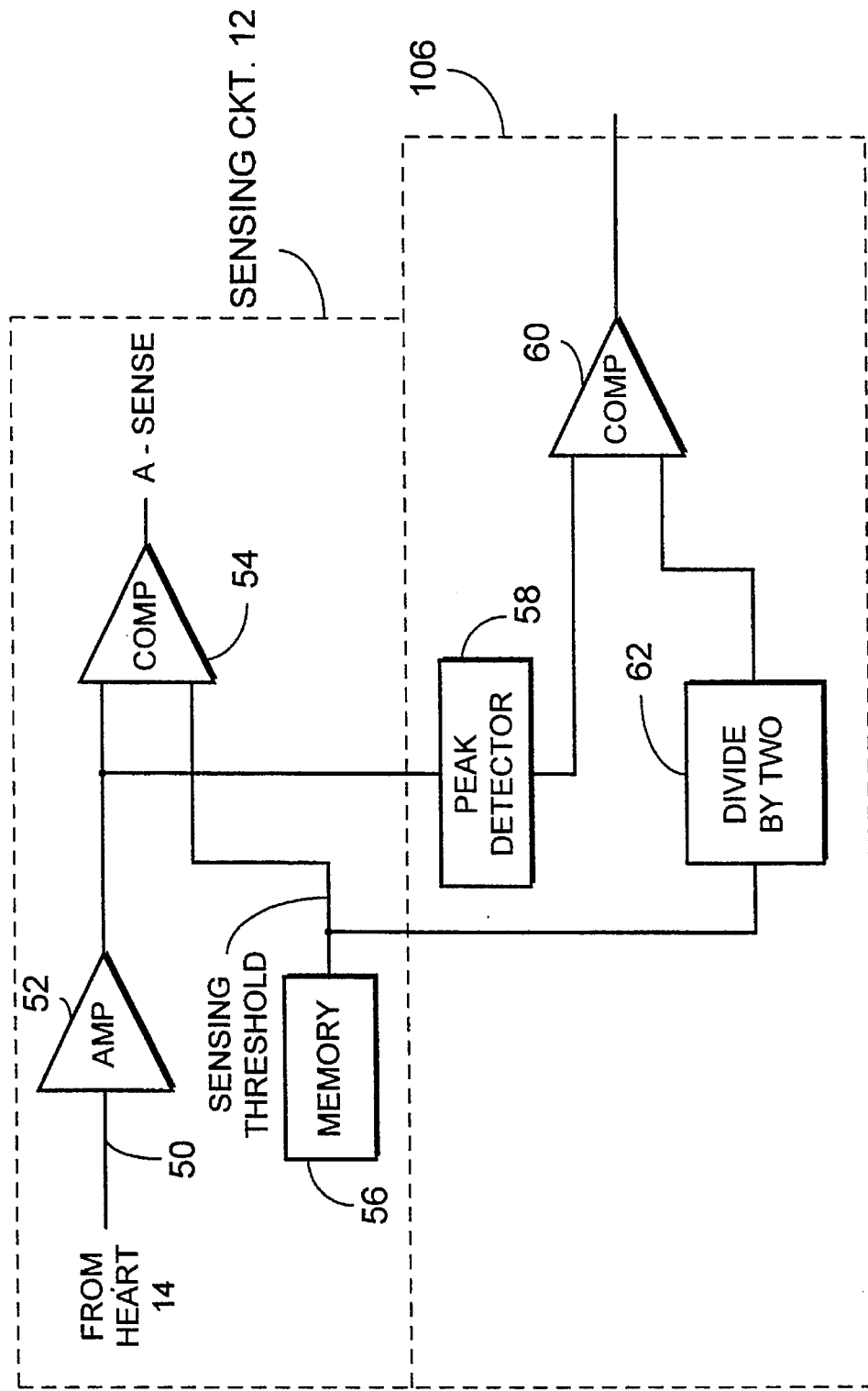
FIG. 8 shows details of a determinator circuit.

Typically, as shown in FIG. 8, in the sensing circuit for sensing the atrium, the atrial electrode 50 is connected to an amplifier 52. The output of amplifier 52 is fed to a comparator 54. The comparator compares the amplified signal sensed on line 50 with a programmable sensing threshold stored in a memory 56. Signals above this threshold are sent as an A-sense signals by the circuit 12. Sensor 106 includes a peak detector 58 which detects the peaks of the signals senses on line 50. These peaks are fed to a comparator 60. The sensor 106 also includes a divide-by-two circuit 62 which receives the sensing threshold from memory 56 and divides by two. The comparator compares the signals on line 50 with the output of circuit 62 and generates an output when the peaks detected by detector 58 fall below this output. This signal is used to determine the Baa signal as discussed above. The threshold (ATH) may be detected at 50% or less than the programmed sensitivity stored in memory 56. The advantage of this approach is that it can automatically determine a high signal to noise ratio of about 2:1.

In the embodiment described above, the ideal or suggested blanking periods are determined by the pacemaker. Alternatively, the calculation to determine the blanking period in the programmer using telemetered ECG's obtained by the pacemaker. Another alternative would be to perform the calculation on the programmer, using the main timing events (MTEs) only. MTEs are marker generated to indicate senses of intracardiac ECGs. In the case, MTEs are markers of noise senses following a paced event.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

What is claimed is:

1. A cardiac stimulation system comprising:

pacing means for generating cardiac pacing signals of a patient;

sensing means for sensing cardiac activity in a cardiac chamber, said sensing means generating sense signals corresponding said cardiac activity;

signal processing means for processing said sense signals;

blanking signal generating means for generating blanking signals, said blanking signals being provided for selectively blanking said signal processing means; and automatic blanking determining means for determining a minimum duration of said blanking signals dependent on physiological characteristics of said heart wherein said automatic blanking determining means includes means for generating a test pacing signal for said heart and test sensing means for sensing activity in said heart responsive to said test pacing signal.

2. The system of claim 1 further comprising an implantable cardiac device, said automatic blanking determining means being disposed in said implantable cardiac device.

3. The system of claim 1 wherein said automatic blanking determining means includes amplitude sensing means for measuring a period from said test pacing signal until said cardiac activity falls below a threshold, said determining means selecting a first blanking signal based on said period.

4. The system of claim 3 wherein said test pacing signal is delivered in a first cardiac chamber and said activity is sensed in a second cardiac chamber to determine a first cross-channel blanking signal.

5. The system of claim 3 wherein said test pacing signal is delivered in a first cardiac chamber and said activity is sensed in said first cardiac chamber to determine a first in-channel blanking period.

6. An implantable cardiac device for implantation in a patient for stimulating the patient's heart, comprising:

pacing means for generating pacing pulses for a first cardiac chamber;

sensing means for sensing cardiac activity in said heart;

blanking means for blanking said sensing means for at least a blanking period following said cardiac activity;

determining means for determining a duration of said blanking period based on a physiology of said heart, wherein said determining means generates a test signal in said first chamber, measures a response to said test signal and determines said duration in accordance with said response.

7. The device of claim 6 wherein said determining means measures said response in said first chamber to determine an in-channel blanking period.

8. The device of claim 7 wherein said first chamber is the atrium.

9. The device of claim 7 wherein said first chamber is the ventricle.

10. The device of claim 6 wherein said determining means measures said response in a second chamber to determine a cross channel blanking period.

11. The device of claim 6 wherein said determining means includes detecting means for detecting a peak of said activity.

12. The device of claim 11 wherein said duration extends from said test signal to a time when said peak falls below a threshold.

13. The device of claim 12 wherein said threshold is a fraction of a maximum peak of said activity.

14. The device of claim 6 wherein said blanking period is set by incrementing said duration a preselected safety margin.

15. The device of claim 14 wherein said safety margin is about 10–30 ms.

16. The device of claim 14 wherein said blanking period is limited to a preselected maximum value.

17. The device of claim 6 wherein said duration is provided to an external programmer used to program said device.

* * * * *